United States Patent [19]
Kane et al.

[11] Patent Number: 5,856,551
[45] Date of Patent: Jan. 5, 1999

[54] MACROMOLECULAR STRUCTURE FOR BORON NEUTRON-CAPTURE THERAPY

[75] Inventors: Robert R. Kane, Los Angeles; M. Frederick Hawthorne, Encino, both of Calif.

[73] Assignee: The Regents of the University of California, Oakland, Calif.

[21] Appl. No.: 810,333

[22] Filed: Feb. 27, 1997

Related U.S. Application Data

[63] Continuation of Ser. No. 371,563, Jan. 11, 1995, abandoned, which is a continuation of Ser. No. 30,920, Mar. 12, 1993, abandoned.

[51] Int. Cl.$^6$ .................................................... C07F 9/09
[52] U.S. Cl. ............................................................ 558/72
[58] Field of Search ................................................ 558/72

[56] References Cited

U.S. PATENT DOCUMENTS

| | | | |
|---|---|---|---|
| 3,444,272 | 5/1969 | Alexander et al. | 558/72 |
| 3,450,798 | 6/1969 | Green et al. | 558/72 |
| 4,399,817 | 8/1983 | Benedict . | |
| 5,272,250 | 12/1993 | Spielvogel et al. | 559/72 X |
| 5,462,724 | 10/1995 | Schinazi et al. | 558/72 X |

OTHER PUBLICATIONS

Paxton, Raymond J.; Beatty, Barbara G.; Varadarajan,, Aravamuthan; and Hawthorne, M. Frederick; "Carboranyl Peptide—Antibody Conjugates for Neutron–Capture Therapy: Preparation, Characterization, and In Vivo Evaluation"; Bioconjugate Chem., vol. 3, 1992, p. 241.

Abraham, R.; Müller; Gabriel, D; "Boronated Antibodies for Neutron Capture Therapy"; Strahlenther. Onkol. 165 (1989), 148–151 (Nr. 2/3).

Barth, R.F.; Mafune, N.; Alam, F.; Adams, D.M.; Soloway, A.H.; Makroglou, G.E.; Oredipe, O.A.; Blue, T.E.; Steplewski, Z.; "Conjugation, Purification and Characterization of Boronated Monoclonal Antibodies for Use in Neutron Capture Therapy"; Strahlenther, Onkol. 165 (1989), 142–145 (Nr. 2/3).

Tamat, S.R.; Patwardhan, A.; Moore, D.E.; Kabral, A.; Bradstock, K.; Hersey, P.; Allen, B.J.; "Boronated Monoclonal Antibodies for Potential Neutron Capture Therapy of Malignant Melanoma and Leukaemia"; Strahlenther. Onkol. 165 (1989), 145–147 (Nr. 2/3).

Varadarajan, Aravamuthan; Hawthorne, M. Frederick; "Novel Carboranyl Amino Acids and Peptides: Reagents for Antibody Modification and Subsequent Neutron–Capture Studies"; Bioconjugate Chem., vol. 2, No. 4, 1991, p. 242.

*Primary Examiner*—Michael G. Ambrose
*Attorney, Agent, or Firm*—Loeb & Loeb LLP; Michael J. Ram; Peter J. Gluck

[57] ABSTRACT

A general synthetic method has been developed for the rapid and efficient production of a variety of boron-rich macromolecules suitable for conjugation with of inclusion in receptor-mediated delivery systems as well as other delivery systems. Preparation techniques have been developed to yield precisely ordered oligophosphates which are soluble, hydrophilic, may be homogeneous, and may be prepared with a variety of functional groups.

5 Claims, No Drawings

MACROMOLECULAR STRUCTURE FOR BORON NEUTRON-CAPTURE THERAPY

This is a continuation application of application Ser. No. 08/371,563 filed on Jan. 11, 1995, abandoned, which is a continuation of application Ser. No. 08/030,920 filed Mar. 12, 1993, abandoned.

BACKGROUND OF THE INVENTION

Boron neutron capture therapy (BNCT) is a binary approach to cancer therapy based on the capture of low-energy neutrons by $^{10}B$, which results in the emission of the cytotoxic $^7Li^+$ nuclei and α-particles ($^{10}B(n,\alpha)^7Li^+$). Tumor-directed antibodies or their immunoreactive fragments are attractive candidates for the selective delivery of $^{10}B$ for BNCT, provided that about 1000 $^{10}B$ atoms can be attached to each immunoreactive protein without significantly altering its biological properties. A number of attempts have been made to link quantities of boron with tumor-directed antibodies, but these have not been succesful in delivering therapeutic quantities of $^{10}B$ to tumor cells. One such attempt proceeded by randomly conjugating whole monoclonal antibodies (Mabs) with large numbers of small boron-containing compounds. Other attempts have been directed to attaching limited numbers of heterogeneous or homogeneous boron-rich polymers. Variability in these studies have limited the progress realized using these techniques.

These studies have also produced disappointing results. For example, an article by Barth, et al., entitled "Conjugation, Purification, and Characterization of Boronated Monoclonal Antibodies for use in Neutron Capture Therapy," describes a delivery system based on attaching a large number of small boron-containing molecules to an antibody. This study indicated that the boronated antibody had a lower level of specificity for tumor tissue than that typical for a native antibody. Studies, using boronated carboranyl peptides, such as that described by Paxton, et al. in an article entitled "Carboranyl Peptide-Antibody Conjugates for Neutron-Capture Therapy: Preparation, Characterization, and in Vivo Evaluation," have also shown a reduced specificity for boronated antibodies.

An article by Varadarajan, et al., entitled "Novel Carboranyl Amino Acids and Peptides: Reagents for Antibody Modification and Subsequent Neutron-Capture Studies," investigated the use of caged boron molecules coupled to peptides. This technique proved unsatisfactory because of excessive hydrophobic bonding between the peptide and the antibody delivery system.

In addition to the poor results obtained using these techniques, these synthesis techniques are frequently slow, sometimes taking weeks to produce a single delivery system. Moreover, if there is to be an eventual commercialization of this technology, a more manufacturable and predictable process must be developed. Little work has been reported on the use of carboranyl derivatives in oligophosphates. One reported use of a carboranyl derivative is in U.S. Pat. No. 4,399,817 to Benedict entitled "Boron Containing Polyphosphonates for the Treatment of Cancer Tumors." The Benedict reference describes the use of boronated polyphosphonates to delivery boron to calcified tumors. Some of the compounds described incorporate carboranyl derivatives, but these compounds only incorporate carboranyl as an end group and not as a monomer within a oligophosphate.

It is therefore an object of the present invention to produce an phosphate-based boron-rich oligomer that is substantially hydrophilic. It is a further object of this invention to develop a synthesis process which utilizes the substantial technical sophistication of standard DNA synthesis techniques.

SUMMARY OF THE INVENTION

One aspect of the present invention relates to a method of preparing a boron-rich oligophosphate including the steps of preparing a dihydroxy carborane derivative; and forming an oligomer structure having at least two dihydroxy carborane derivatives as monomer units.

Another aspect of the present invention relates to a boron-rich oligophosphate which includes at least two dihydroxy carborane derivates as monomer units.

Another aspect of the present invention relates to a method of coupling $^{10}B$ with a tumor targeting delivery vehicle for BNCT of cancer, comprising the steps of preparing an oligomer having at least two dihydroxy carborane derivatives as monomer units and coupling the oligomer with a preselected tumor targeting vehicle.

DETAILED DESCRIPTION OF THE INVENTION

The present invention is directed to the use of boron-rich oligophosphates in boron neutron-capture therapy (BNCT) of cancer. Although a number of the embodiments of the present invention are described in terms of preparing an antibody-based delivery vehicle, the present invention is also directed to the use of boron-rich oligophosphates without a delivery vehicle, and to the use of boron-rich oligophosphates with a variety of other delivery vehicles.

By way of terminology, the terms closo-carborane, o-carborane, or carboranyl refer to derivatives of the closo-$1,2-C_2B_{10}H_{12}$ cage, while nido-carborane refers to derivatives of the $[nido-7,8-C_2B_9H_{11}]^-$ cage fragment.

Solution Synthesis

The present invention is directed to the use of derivatives of o-carborane (structure 1) and one aspect of the present invention utilizes these relatively stable boron-rich compounds

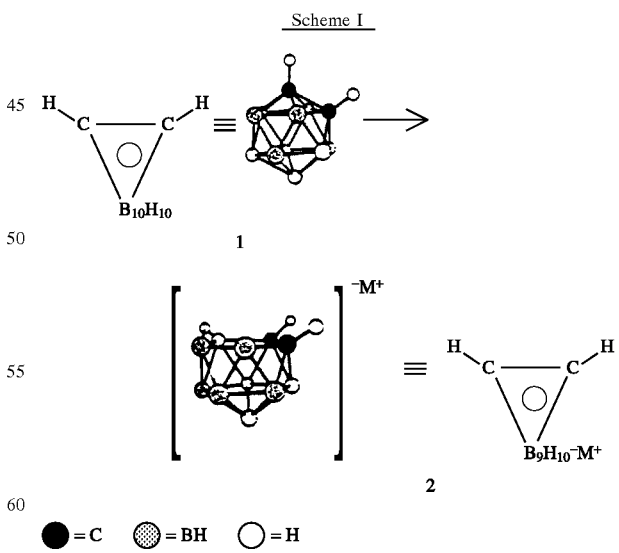

because they can be readily functionalized. Synthesis of the carboranes is described in Grimes, *Carboranes*, (1970), which is herein incorporated by reference. In accordance with another aspect of the present invention, lipophilic closo-carborane derivatives are converted under mild conditions to stable anionic nido-carborane derivatives (structure 2, Scheme 1) which exhibit enhanced hydrophilicity. The papers by Hawthorne, et al., *Inorg. Chem.*, 4, 1675 (1965), and by Wiesbock, et al., *J. Am. Chem. Soc.* 86, 1643–1644, describe this synthesis process and are herein incorporated by reference. With reference to Scheme II, oligophosphates formed in accordance with one aspect of the present invention are derived from the structure 3, or o-carborane diol, which can be prepared by the condensation of dilithio-o-carborane with an excess of trimethylene oxide (yield=90%).

Treatment of the structure 3 diol with one equivalent of TBDMSOTf (tert-butyldimethylsilyltrifluoromethanesulfonate) affords the structure 4 molecule (at a 48% yield by Scheme II) after chromotographic purification of the statistically protected mixture. Materials removed in the chromatographic purification process included a mixture of mono- and diprotected products and

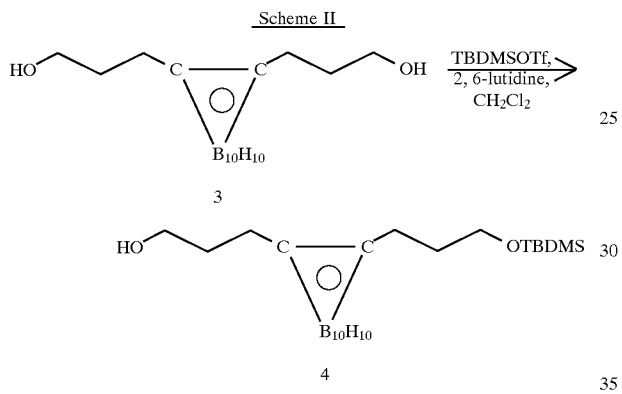

unreacted diol. The coupling of the structure 4 monoprotected o-carboranyl diol with isobutanol was then examined under a variety of conditions (Scheme IV). The experimental results of these coupling reactions are summarized in Table I. The simplicity, speed, economy and efficiency of the dichlorophosphite coupling reaction (entry #4 of Table I) indicate that this method is a preferred embodiment of the present invention.

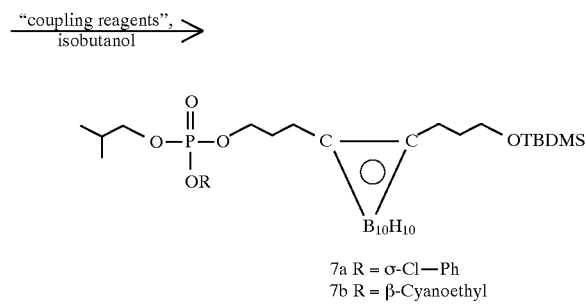

TABLE I

Yields for the Synthesis of the Structure 5 Compound Under Various Conditions.

| Entry | Coupling Reagent | R | Yield |
|---|---|---|---|
| 1 | $Cl_2P(O)OR$ | $2\text{-}ClC_6H_2$ | 25% |
| 2 | $(BTO)_2P(O)OR^a$ | " | 47% |
| 3 | $Cl_2POR^b$ | " | 68% |
| 4 | $Cl_2POR^c$ | " | 88% |
| 5 | $ClP(OR)N(i\text{-}Pr)_2^{d,e}$ | $NC(CH_2)2\text{-}$ | 54%[e] |

Notes:
[a] BT = benzotriazole;
[b] The initially formed phosphite triester was oxidized in situ with aqueous iodine (0.1M);
[c] The initially formed phosphite triester was oxidized in situ with 0.1M iodine in $THF/H_2O/2,5$-Lutidine (40/1/10);
[d] The intermediate phosphoramidite was isolated in 90% yield, and was coupled with isobutanol in the presence of tetrazole;
[e] Yield from two steps.

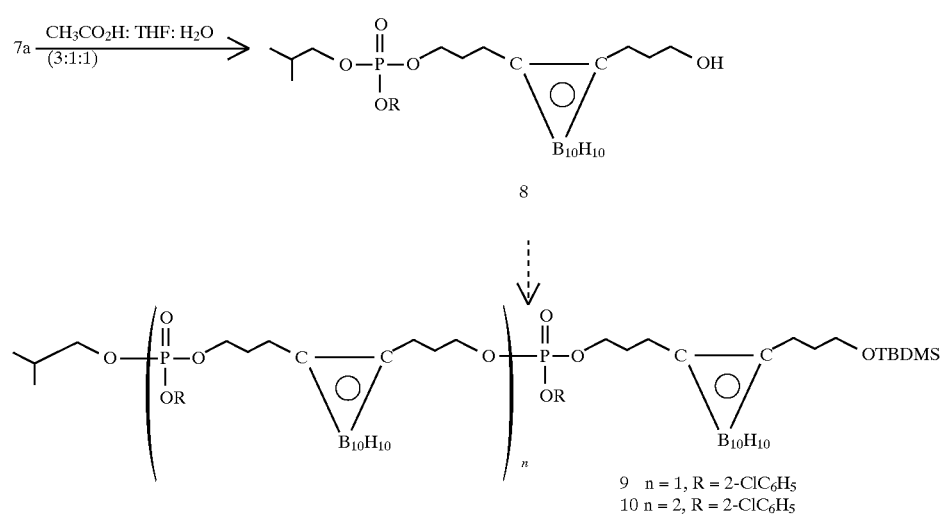

In accordance with an aspect of the present invention, reaction of the monoprotected o-carboranyl diol 4 with isobutanol under a variety of conditions yields the structure 7 phosphotriester. The structure 7a phosphotriester may be converted under acidolytic conditions to the structure 8 alcohol. The structure 8 alcohol may be condensed with another portion of the structure 4 alcohol (monoprotected diol) to produce the structure 9 diphosphate at a moderate yield (35% from two steps, Scheme IV). A second iteration of deprotection and coupling provided the structure 10 triphosphate in a low but reproducible yield (18% from two steps). This process may also be performed by employing a hydroxyl protecting group other than the tert-butyldimethylsilyl group. For example, in a preferred embodiment of the present invention, a relatively labile protecting group such as dimethoxytrityl may be used.

In accordance with another aspect of the present invention,

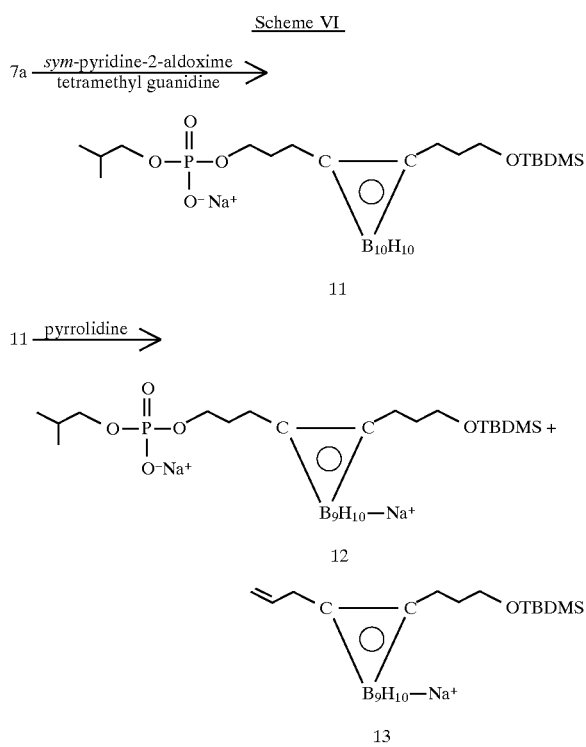

the phosphate-protecting groups may be removed from these structures, and the closo-carboranes can be converted to the anionic nido-derivatives. Removal of the phosphate-protecting groups is done under the standard conditions that are well known to one of ordinary skill in the art. By examining the reactions of the structure 7a monophosphate in a model study, we found that the 2-chlorophenyl phosphate-protecting group could be efficiently removed under standard conditions. Accordingly, treatment of the structure 7a compound with syn-pyridine-2-aldoxime and tetramethylguanidine in THF at room temperature followed by a cation exchange ($Na^+$ form cation exchange resin) afforded the structure 11 sodium salt at an 87% yield (Scheme V). When this anion was suspended in neat-pyrrolidine at room temperature (1 hr) the closo-carborane was converted to the nido-carboranyl phosphate at a 71% crude yield (structure 12, Scheme V). A small amount of the structure 13 alkene appears to have also been isolated in this process. Milder conditions would afford substantially higher yields. The isolation of the structure 12 phosphate, which is extremely hydrophilic, demonstrates the utility of the present invention's approach to the synthesis of boron-rich macromolecules.

Experimental Discussion of Solution Synthesis $^1H$ NMR spectra were recorded on a Bruker AF-200 spectrometer, operating at 200.132 MHz or a Bruker AM-360 spectrometer, operating at 360.134 MHz. $^{13}C$ NMR spectra were also recorded on the AF-200 and AM-360, operating at 50.323 and 90.556, respectively. $^{11}B$ NMR spectra were recorded on a Bruker AM-500 spectrometer operating at 160.463 MHz. $^{31}P$ NMR spectra were recorded on the AM-360 operating at 145.785 MHz. Infrared spectra were recorded on a Beckman FTIR spectrometer as a liquid film (neat) or a Nujol mull. Melting points were obtained on a Thomas Hoover "uni-melt" capillary melting point apparatus. HI-RES FAB mass spectra were performed by the University of California at Riverside Mass Spectrometry Facility and obtained on a VG Analytical ZAB mass spectrometer using a m-nitrobenzyl alcohol matrix.

$^1H$ NMR, $^{13}C$ NMR, $^{11}B$ and $^{31}P$ are reported in parts per million (δ). The following abbreviations are used: s=singlet; d=doublet; t=triplet; q=quartet; and m=multiplet. IR data are reported in wave numbers ($cm^{-1}$). The following abbreviations are used to indicate qualitative intensities: vs=very strong; s=strong; m=medium; w=weak; and br=broad.

Thin layer chromatography (TLC) was performed using plates from EM Science (silica gel 60 F254; layer thickness 0.2 mm). Visualization was accomplished using ultraviolet light and/or by staining with an aqueous potassium permanganate solution (5.0 g $KMnO_4$, 20 g $K_2CO_3$, 5.0 mL 5% NaOH, 300 mL $H_2O$). Separation via flash column chromatography was possible using a 6 inch column (3 inch diameter) of silica gel (grade 60, 230–400 mesh, 60 A). Solvent systems were reported as volume percent mixtures. All reagents were obtained from commercial sources and were used without further purification unless otherwise noted.

EXAMPLE 1

Di-O-tert-butyldimethylsilyl-bis-hydroxypropyl-ortho-carborane and O-tert-butyldimethylsilyl-bis-hydroxypropyl-ortho-carborane 4

Under nitrogen, 0.100 g (0.380 mmol) of bis-hydroxypropyl-ortho-carborane 3 was dissolved in a 1:1 solvent mixture of dry methylene chloride and dry diethyl ether at room temperature. Next, 0.0400 mL (0.380 mmol) of 2,6-lutidine and 0.0900 mL (0.380 mmol) of tert-butyldimethylsilyl trifluoromethanesulfonate 98% were added. The reaction mixture was stirred at room temperature for two hours before being quenched with saturated $NaHCO_3$. The resulting aqueous mixture was then extracted twice with ether. The ether extracts were collected, dried over $MgSO_4$, filtered and concentrated on the rotary evaporator. The resulting residue was next purified by flash chromatography using a solvent system which consisted of EtOAc:Hexanes 1:1. In this manner, 0.039 g (0.0799 mmol, 21.0%) of the diprotected product ($R_f$=0.8), m.p. 108°–110° C., and 0.068 g (0.182 mmol, 47.9%) of the monoprotected product 4 ($R_f$=0.5), m.p. 49°–51° C., were isolated. Final elution of the flash column with ethanol allowed for the recovery of starting material 3.

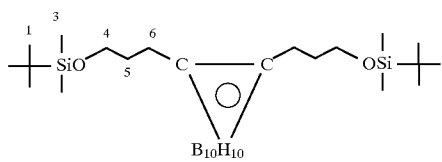

360 MHz $^1$H NMR (CDCl$_3$) δ (ppm): 0.0338 (s, 12H, H-3), 0.874 (s, 18H, H-1), 1.69–1.77 (m,4H, H-5), 2.24–2.29 (m, 4H, H-6), 3.59 (t, 4H, J=5.7 Hz, H-4).

90 MHz $^{13}$C NMR (CDCl$_3$) δ (ppm): 79.71, 61.62, 32.76, 31.72, 25.83, 18.18, 13.72

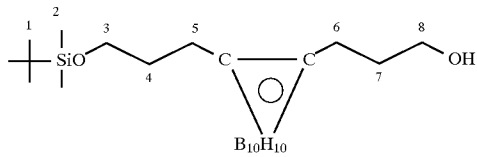

360 MHz $^1$H NMR (CDCl$_3$) δ (ppm): 0.0316 (s, 6H, H-2), 0.868 (s, 9H, H-1), 1.69–1.75 (m, 2H, H-7), 1.76–1.82 (m, 2H, H-4), 2.26–2.32 (m, 4H, H-5 and H-6), 3.60 (t, 2H, J=5.7 Hz, H-3), 3.63 (dd, 2H, J=5.6 Hz, J=9.9 Hz, H-8).

90 Mhz $^{13}$C NMR (CDCl$_3$) δ (ppm): 79.73, 79.49, 61.59, 61.45, 32.71, 32.42, 31.67, 31.59, 25.80, 18.15, 14.14

IR (nujol): 3356 (br) cm$^{-1}$, 2589 (s) cm$^{-1}$, 1256 (s) cm$^{-1}$, 1387 (br) cm$^{-1}$ NEGATIVE HI-RES FAB-MS for C$_{14}$H$_{38}$B$_{10}$O$_2$Si: m/e 376.3571[M−]. Found: m/e 376.3584. Δ=1.2 mmu (3.3 ppm)

Protected monophosphate 7a:

The compound 7a was synthesized following the method proposed by R. L. Letsinger, et al. Under nitrogen, 0.092 mL (0.590 mmol) of 2-chlorophenyl dichlorophosphite was added to a dry 50 mL schlenk flask cooled to −78° C. In a separate flask, 4 was dissolved in dry THF (10 mL) before 0.224 mL (1.90 mmol) of 2,6-lutidine was added. The resulting THF mixture was then added dropwise to the phosphite and stirred at −78° C. for 10 minutes. Then 0.059 mL (0.640 mmol) of isobutanol was added and stirred for 20 minutes at −78° C. after which it was allowed to stir at room temperature for 5 minutes. Next an excess of 0.1M I$_2$ (3.05 g in THF:pyridine:H$_2$O; 80:40:2) was added. This mixture was then extracted twice with 100 mL aliquots ether. The ether layers were then washed with 10% Na$_2$S$_2$O$_3$ followed by saturated NaCl. Next the organic layers were collected, dried over MgSO$_4$ and filtered. The ether solvent was stripped off on the rotary evaporator to give a yellow residue which was purified on flash silica gel using a solvent system which consisted of EtOAc:Hexanes 1:1. In this manner, 0.290 g (0.468 mmol, 88.3%) of the desired product 7a (R$_f$=0.5) was recovered as a yellow oil.

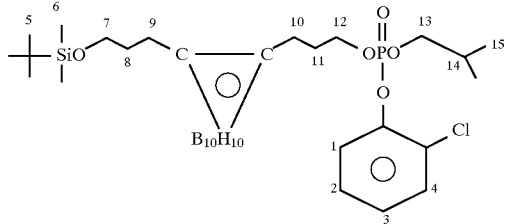

360 Mhz $^1$H NMR (CDCl$_3$) δ (ppm): 0.0264 (s, 6H, H-6), 0.863 (s, 9H, H-5), 0.942 (d, 6H, J=6.7 Hz, H-15), 1.66–1.76 (m, 1H, H-14), 1.90–2.01 (m, 4H, H-8 and H-11), 2.22–2.30 (m, 4H, H-9 and H-10), 3.58 (t, 2H, J=5.7 Hz, H-7), 3.96 (td, 2H, J=2.7 Hz, J=6.5 Hz, H-12), 4.18 (dd, 2H, J=6.0 Hz, J=13.0 Hz, H-13), 7.13 (t, 1H, J=7.6 Hz, H-3), 7.25 (t, 1H, J=7.6–8.0 Hz, H-2), 7.42 (d, 1H, J=8.1 Hz, H-4), 7.43 (d, 1H, J=8.1 Hz, H-1).

90 MHz $^{13}$C NMR (CDCl$_3$) δ (ppm): 146.6, 130.7, 127.9, 126.0, 125.3, 121.3, 79.71, 78.61, 74.99, 74.92, 67.23, 67.16, 61.48, 32.77, 31.65, 31.21, 30.22, 30.14, 29.05, 28.97, 25.80, 18.51, 18.15, 13.74

IR (neat): 2594 (s) cm$^{-1}$, 1259 (s) cm$^{-1}$

FAB-MS for C$_{24}$H$_{50}$B$_{10}$ClO$_5$PSi: m/e 621 [M+1]

Hydroxy monophosphate 8:

The deprotection of 7a afforded compound 8.$^3$ 0.211 g (0.340 mmol) of 7a was suspended in acetic acid-water-tetrahydrofuran (3:1:1). The reaction mixture was allowed to stir at room temperature until 7a went into solution. The reaction was quenched thoroughly with saturated NaHCO$_3$ and then extracted twice with 200 mL aliquots of ether. The ether extracts were then collected, dried over MgSO$_4$, filtered and concentrated on the rotary evaporator. The resulting residue was purified using flash chromatography. The column was first eluted with EtOAc:Hexanes 1:1. Next the same column was eluted with 100% EtOAc. Concentration of the fractions from the second elution gave 0.117 g (0.231 mmol, 68.0%) of 8 as a yellow oil.

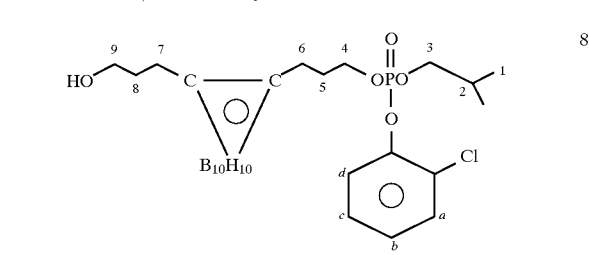

360 MHz $^1$H NMR (CDCl$_3$) δ (ppm): 0.941 (d, 6H, J=6.7 Hz, H-1), 1.66–1.77 (m, 1H, H-2), 1.92–2.07 (m, 4H, H-5 and H-8), 2.31–2.37 (m, 4H, H-6 and H-7), 3.59 (t, 2H, J=5.4 Hz, H-9), 3.95 (td, 2H, J=2.9 Hz, J=6.5 Hz, H-4), 4.22 (dd, 2H, J=2.8 Hz, J-7.0 Hz, H-3), 7.15 (t, 1H, J=7.8 Hz, H-b), 7.26 (t, 1H, J=8.0 Hz, H-c), 7.41 (d, 1H, J=8.3 Hz, H-a), 7.43 (d, 1H, J=8.2 Hz, H-d).

90 Mhz $^{13}$C NMR (CDCl$_3$) δ (ppm): 146.7, 130.7, 128.0, 126.2, 125.5, 121.3, 79.97, 78.42, 75.21, 75.13, 67.58, 61.25, 32.69, 31.91, 31.04, 30.20, 29.05, 18.49

145 MHz $^{31}$P NMR (CDCl$_3$) δ (ppm):
External Reference H$_3$PO$_4$/D$_2$O −9.220
External Reference H$_3$PO$_4$/CDCl$_3$ −6.584

IR (neat): 2584 (s) cm$^{-1}$, 1263 (s) cm$^{-1}$

HI-RES FAB-MS for C$_{18}$H$_{36}$B$_{10}$ClO$_5$P: m/e 508.2919 [M−]. Found: m/e 508.289. Δ=3.2 mmu (6.4 ppm).

Protected diphosphate 9:

The compound 9 was synthesized in a manner similar to that of 7a.$^2$ 0.051 mL (0.330 mmol) of 2-chlorophenyl dichlorophosphite was placed in a schlenk flask, under nitrogen, and cooled to −78° C. In a separate flask, 0.151 g (0.290 mol) of 8, dissolved in 10 mL dry THF, and 0.125 mL (1.10 mmol) of 2,6-lutidine were combined and added dropwise to the phosphite. The resulting mixture was stirred at −78° C. for 10 minutes before 0.134 g (0.360 mmol) of 4 in dry THF was added and stirred 20 minutes longer before the cold bath was removed. After 5 minutes, an excess of 0.1M I$_2$ (3.05 g in pyridine:THF:H$_2$O; 40:80:2) was introduced. Extraction with ether followed. The ether extracts were washed once with 10% Na$_2$S$_2$O$_3$, once with saturated NaCl, dried over MgSO$_4$ and filtered. Solvent ether was then stripped off under reduced pressure. The crude product was chromatographed on flash silica gel using a solvent system of EtOAc:Hexanes 1:1. In this manner, 0.155 g (0.147 mmol, 50.8%) of the desired product 9 was isolated.

360 MHz $^1$H NMR (CDCl$_3$) δ (ppm): 0.0252 (s, 6H, H-16), 0.862 (s, 9H, H-17), 0.936 (d, 6H, J=6.6 Hz, H-1), 1.63–1.75 (m, 1H, H-2), J=6.5 Hz, H-4), 4.19 (dd, 6H, J=6.6 Hz, J=12.7 Hz, H-3, H-9 and H-10), 7.16 (dd, 2H, J=7.8 Hz, J=16.0 Hz, H-c and H-g), 7.27 (dd, 2H, J=6.8 Hz, J=15.0 Hz, H-b and H-f), 7.36–7.45 (m, 4H, H-a, H-d, H-e and H-h).

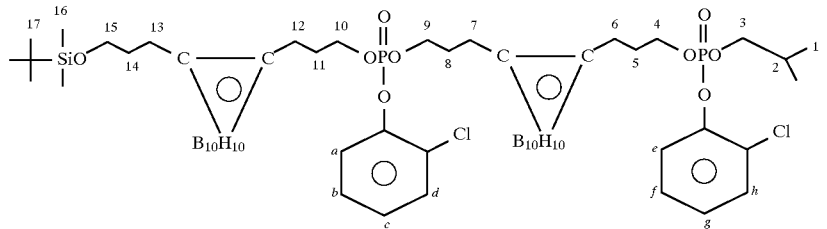

1.92–2.05 (m, 8H, H-5, H-8, H-11 and H-14), 2.17–2.31 (m, 8H, H-6, H-7, H-12 and H-13), 3.57 (t, 2H, J=5.7 Hz, H-15), 3.95 (td, 2H, J=2.7 Hz, J=6.6 Hz, H-4), 4.17 (dd, 6H, J=6.0 Hz, J=10.1 Hz, H-3, H-9 and H-10), 7.15 (dd, 2H, J-7.8 Hz, J=18 Hz, H-c and H-g), 7.26 (dd, 2H, J=6.3–6.7 Hz, J=14 Hz, H-b and H-f), 7.42 (d, 4H, J=8.0 Hz, H-a, H-d, H-e and H-h).

90 MHz $^{13}$C NMR (CDCl$_3$) δ (ppm): 146.3, 146.2, 130.8, 130.7, 128.1, 128.0, 126.4, 126.1, 125.3, 125.2, 121.4, 121.3, 79.72, 78.62, 78.49, 78.04, 75.05, 74.97, 67.57, 67.50, 67.44, 67.37, 67.19, 67.12, 61.46, 32.77, 31.64, 31.19, 31.06, 30.23, 30.16, 29.68, 29.05, 28.97, 25.82, 18.52, 18.16, 14.10

145 MHz $^{31}$P (CDCl$_3$) δ (ppm):

External Reference H$_3$PO$_4$/CDCl$_3$ −5.63, −5.66

NEGATIVE FAB-MS for C$_{38}$H$_{76}$B$_{20}$Cl$_2$O$_9$P$_2$Si: m/e 1053

Hydroxy diphosphate:

This compound was prepared in the same manner as 8.[3] 0.176 g (0.167 mmol) of 9 was suspended in 100 mL of CH$_3$COOH:THF:H$_2$O 3:1:1 and stirred at room temperature until all was in solution. The reaction was quenched with saturated NaHCO$_3$ and extracted with ether. The ether extracts were collected, dried over MgSO$_4$ and filtered. The solvent ether was then removed. The crude product was purified on flash silica gel. The column was first eluted with EtOAc:Hexanes 1:1 and then with 100% EtOAc. Concentration of the EtOAc fractions afforded 0.099 g (0.105 mmol, 63.1%) of the desired compound as a yellow oil.

90 MHz $^{13}$C NMR (CDCl$_3$) δ (ppm): 146.5, 146.2, 130.8, 130.7, 128.2, 128.0, 126.5, 126.1, 125.3, 125.2, 121.5, 121.3, 79.88, 78.60, 78.54, 78.42, 75.10, 67.80, 67.73, 67.59, 67.27, 60.98, 32.56, 31.79, 31.12, 30.97, 30.15, 30.09, 28.99, 28.91, 28.51, 18.44

145 Mhz $^{31}$P NMR (CDCl$_3$) δ (ppm):

External Reference H$_3$PO$_4$/D$_2$O −8.874, −8.454, −8.662, −8.694, −8.763

IR (neat): 3462 (br) cm$^{-1}$, 2593 (s) cm$^{-1}$, 1234 (s) cm$^{-1}$

NEGATIVE HI-RES FAB-MS for C$_{32}$H$_{62}$B$_{20}$Cl$_2$O$_9$P$_2$: m/e 942.5107 Found: m/e 942.513. Δ=2.4 mmu (2.5 ppm).

Triphosphate 10:

The compound 10 was synthesized in a manner similar to that of 9.[2] In a schlenk flask, 0.017 mL (0.110 mmol) of 2-chlorophenyl dichlorophosphite was cooled to −78° C. under nitrogen. 0.095 g (0.100 mmol) of the hydroxy diphosphate was dissolved in 5 mL dry THF before 0.042 mL (0.360 mmol) of 2, 6-lutidine was added. This THF solution was then added dropwise to the phosphite and stirred at −78° C. for 5 minutes. Next 0.045 g (0.120 mmol) of 4 dissolved in 5 mL dry THF was added and stirred at −78° C. for 20 minutes. The reaction mixture was then allowed to stir at room temperature for 5 minutes before an excess of 0.1M I$_2$ (3.05 g in THF:pyridine:H$_2$O; 80:40:2) was added. The resulting solution was extracted with ether. The ether extracts were then washed with 10% Na$_2$S$_2$O$_3$ and saturated NaCl, dried over MgSO$_4$ and filtered. After the solvent was removed, the crude product was columned on

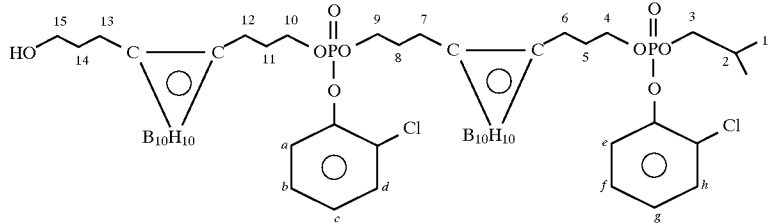

360 MHz $^1$H NMR (CDCl$_3$) δ (ppm): 0.939 (d, 6H, J=6.5 Hz, H-1), 1.66–1.74 (m, 1H, H-2), 1.86–2.07 (m, 8H, H-5, H-8, H-11 and H-14), 2.17–2.33 (m, 8H, H-6, H-7, H-12 and H-13), 3.55 (t, 2H, J=5.7 Hz, H-15), 3.95 (td, 2H, J=2.2 Hz, flash silica gel. The column was first eluted with EtOAc:Hexanes 1:1 and then 100% EtOAc. Concentration of the EtOAc fractions gave 0.042 g (0.028 mmol, 28.3%) of 10 as a yellow oil.

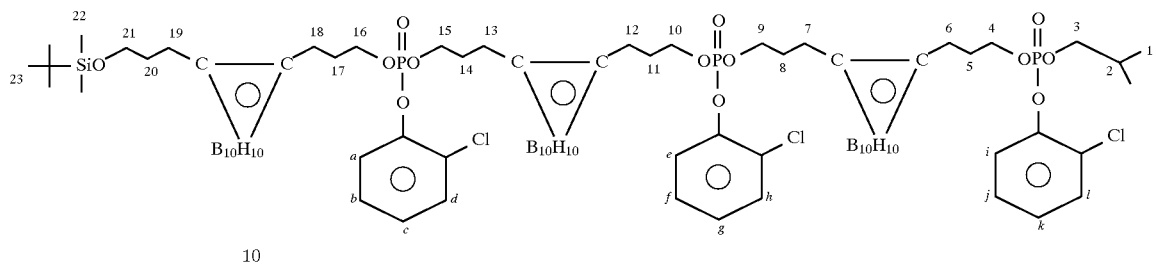

360 MHz $^1$H NMR (CDCl$_3$) δ (ppm): 0.0252 (s, 6H, H-22), 0.861 (s, 9H, H-23), 0.933 (d, 6H, J=6.7 Hz, H-1), 1.67–1.75 (m, 1H, H-2), 1.83–2.03 (m, 12H, H-5, H-8, H-11, H-14, H-17 and H-20), 2.17–2.31 (m, 12H, H-6, H-7, H-12, H-13, H-18 and H-19), 3.57 (t, 2H, J=5.7 Hz, H-21), 3.95 (d, 2H, J=2.6 Hz, J=6.6 Hz, H-4), 4.15–4.20 (m, 10H, H-3, H-9, H-10, H-15 and H-16), 7.13–7.18 (m, 3H, H-c, H-g and H-k), 7.23–7.29 (M, 3H, H-b, H-f and H-j), 7.39–744 (m, 6H, H-a, H-d, H-e, H-h, H-i and H-l).

90 MHz $^{13}$C NMR (CDCl$_3$) δ (ppm): 146.3, 146.7, 130.8, 130.7, 128.4, 128.2, 128.0, 126.5, 126.1, 125.3, 121.5, 121.4, 78.64, 78.53, 75.06, 74.99, 67.53, 67.14, 61.47, 32.76, 31.65, 31.16, 31.03, 30.20, 30.13, 29.05, 28.97, 25.81, 18.51, 14.11

145 MHz $^{31}$P NMR (CDCl$_3$) δ (ppm):
External Reference H$_3$PO$_4$/D$_4$D$_2$O −8.212, −8.240, −8.258

NEGATIVE FAB-MS for C$_{52}$H$_{102}$B$_{30}$Cl$_3$O$_{13}$P$_3$Si: m/e 1488 [M−].

Anionic monophosphate 11:
Deprotection of 7a provided compound 11.[4] 0.0116 g (0.950 mmol) of 2-pyridinealdoxime and 0.120 mL (0.820 mmol) of 1,1,3,3-tetramethyl guanidine were dissolved in 2.87 mL of dry dioxane:acetonitrile (1:1). This solution was then added to 7a (0.115 g, 0.190 mmol). The reaction mixture was allowed to stir at room temperature for 28 hours. Next Bio. RAD. AG50W-x8 ion-exchange resin (50–100 mesh; 22 g) ammonium form was added and stirred for 30 minutes. The resin was then filtered off and washed with tetrahydrofuran. The THF was removed under vacuum. The resulting residue was then purified on flash silica gel. The column was first eluted with CHCl3:MeOH 8:2 followed by 100% MeOH. In this manner, 0.070 g (0.133 mmol, 71.4%) of 11 was formed.

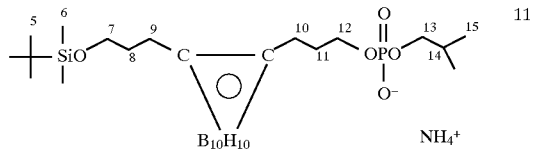

360 MHz $^1$H NMR (CDCl$_3$) δ (ppm): 0.0460 (s, 6H, H-6), 0.878 (s, 9H, H-5), 0.918, (d, 6H, J=6.2 Hz, H-15), 1.70–1.90 (br m, 5H, H-8, H-14 and H-11), 2.16–2.43 (br m, 4H, H-9 and H-10), 3.52–3.69 (br m, 4H, H-7 and H-12), 3.77–3.91 (br m, 2H, H-13).

90 MHz $^{13}$C NMR (CDCl$_3$) δ (ppm): 80.10, 79.10, 72.80, 64.80, 61.60, 33.19, 31.91, 30.14, 29.35, 26.72, 25.87, 19.13, 18.19, 14.11

145 MHz $^{31}$P NMR (CDCl$_3$) δ (ppm):
External Reference H$_3$PO$_4$/D$_2$O −4.238
160 MHz $^{11}$B NMR δ (ppm): −4.336, −9.860
NEGATIVE HI-RES FAB-MS for C$_{18}$H$_{46}$B$_{10}$O$_5$PSi: m/e 511.3782 [M−]. Found: m/e 511.3808. Δ=2.5 mmu (4.9 ppm).

nido-Anionic monophosphate 12:
Degradation of closo-11 with pyrrolidine provided nido-12.5 0.070 g (0.133 mmol) of 11 was treated with 0.570 mL (6.83 mmol) of pyrrolidine and stirred at room temperature for one hour. Afterwards, the pyrrolidine was removed in vacuo. The resulting residue proved to be the pyrrolidinium salt of nido-12 (0.055 g, 0.093 mmol, 70.5% crude).

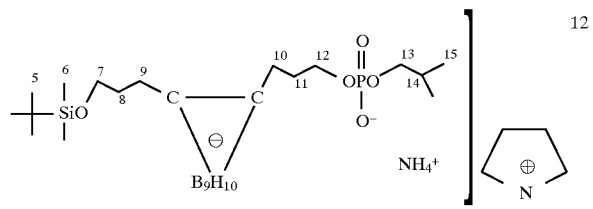

3.60 MHz $^1$H MR (CDCl$_3$) δ (ppm): 0.0122 (s, 6H, H-6), 0.857 (s, 9H, H-5), 9.907 (d, 6H, J=6.7 Hz, H-15), 1.59–1.71 (m, 1H, H-14), 1.75–1.90 (m, 4H, H-8 and H-11), 1.96–2.03 (m, 4H, H-9 and H-10), 3.21 (t, 2H, J=6.8 Hz, H-7), 3.50–3.54 (m, 2H, H-12), 3.67–3.79 (m, 2H, H-13).

90 MHZ $^{13}$C NMR (CDCl$_3$) δ (ppm): 72.20, 65.30, 53.68, 31.89, 30.84, 30.33, 29.32, 26.70, 25.97, 19.04, 18.30, 14.08

145 MHz $^{31}$P NMR (CDCl$_3$) δ (ppm):
External Reference H$_3$PO$_4$/D$_2$O −1.246
160 MHz $^{11}$B NMR (CDCl$_3$) δ (ppm): −11.23, −17.77, −34.76, −37.55

NEGATIVE HI-RES FAB-MS for C$_{18}$H$_{46}$B$_9$O$_5$PSi: m/e 500.3689 [M−]. Found: m/e 500.3714. Δ=2.4 mmu (4.9 ppm).

General DNA Synthesis
The chemical synthesis of DNA customarily involves the repetitive coupling of suitably functionalized nucleosides, with the growing polymer remaining attached to a solid support throughout the synthesis. Each step of this synthesis has been extensively studied, resulting in the development of an overall procedure that is fast (just minutes per monomer), efficient (coupling efficiency routinely >99%), and amenable to automation. Techniques for automated DNA synthesis are well known in the art and are described in, for example, Gait, M. J. (ed.) Oligonucleotide Synthesis: A Practical Approach, (1984), which is herein incorporated by reference. A general scheme for the most common method of DNA synthesis, using β-cyanoethyl protected diisopropylaminophosphoramidites, is shown below (Scheme 1). In general, this method involves:

a) removal of an —OH protecting group from a polymer supported monomer;

b) coupling of the resulting free —OH with a protected diisopropylaminophosphoramidite utilizing tetrazole as an acid catalyst;

c) oxidation of the initially formed phosphite triester to form the phosphate triester;

d) acetate ester formation on unreacted —OH groups (blocking);

e) acid deprotection of the newly introduced dimethoxytrityl ether protecting groups;

f) repetition of steps (b)–(f) until complete oligomer has been assembled; and g) removal of oligomer from the solid support using NH$_4$OH, with concomittant removal of the phosphate protecting groups.

This method can be readily adapted for use with other phosphoramidites (dimethylamino etc.), different phosphate In general, however, Scheme 1 describes the most common method of DNA synthesis.

In accordance with an aspect of the present invention, the DNA synthesis chemistry described in Scheme 1 has the general requirements a candidate monomer for this method of oligophosphate synthesis should contain both a dimethoxytrityl protected alcohol and a β-cyanoethyl-diisopropylaminophosphoramidite. A schematic of oligophosphate synthesis in accordance with an aspect of the present invention involving a

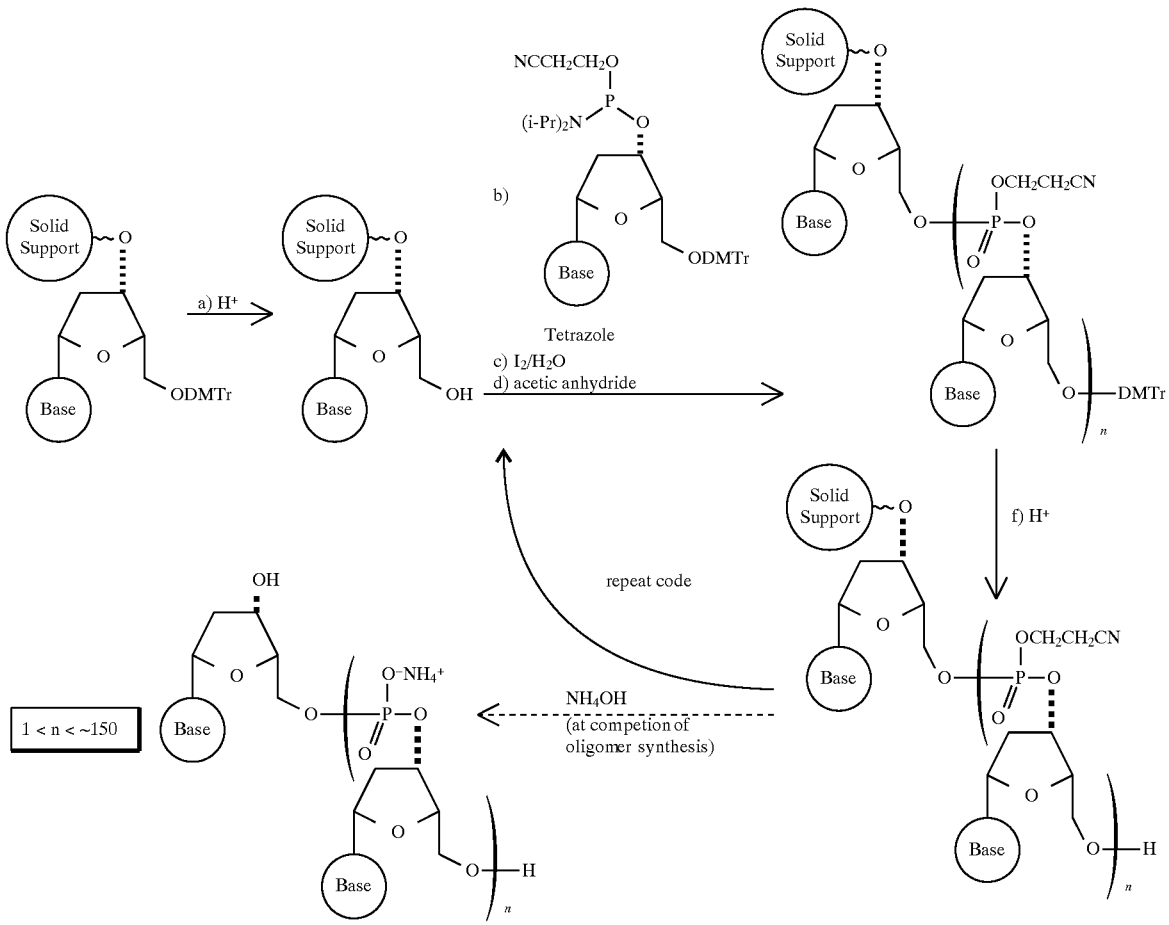

protecting groups (methoxy vs. β-cyanoethyl), and alternate activation/oxidation strategies (H-phosphonate chemistry).

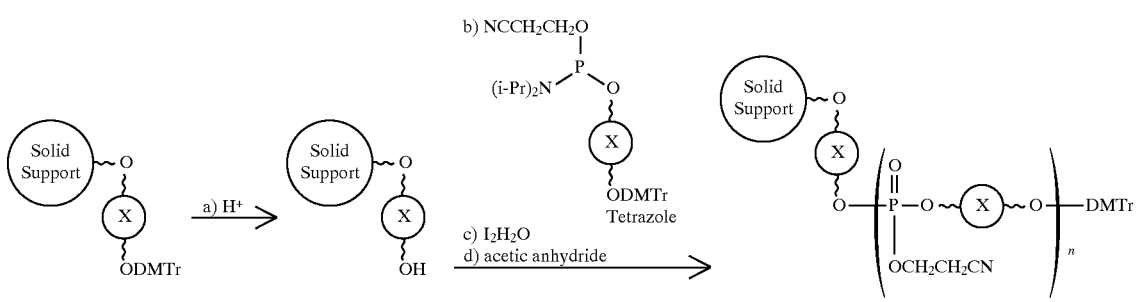

-continued
Scheme 2

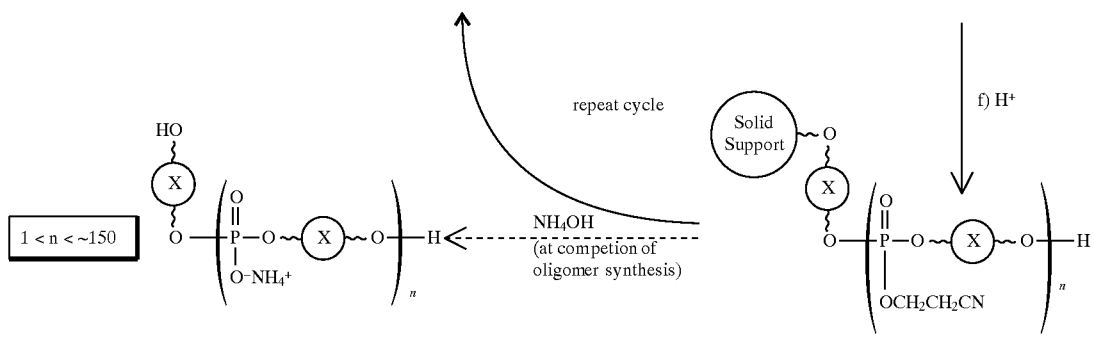

generalized monomer is shown in Scheme 2.

Solid-Phase Boron-Rich Oligomer Synthesis

Boron-rich oligophosphates were synthesized on a one micromole scale using a Applied Biosystems DNA Synthesizer, Model 391. Standard concentrations of reagents were used: The monomer was dissolved to a concentration of 0.1M in $CH_3CN$; the deprotecting solution was 3% trichloroacetic acid in dichloromethane; the capping solutions wer an 8:1:1 mixture of THF:lutidine:acetic anhydride and 1.2% dimethylaminopyridine in THF; the oxidant was 0.5M $I_2$ in methanol, pyridien and water (7:2:1). All steps were of standard duration; for example, the coupling time was 15 seconds.

Oligomers containing up to 40 carboranyl monomers were synthesized with coupling efficiencies of greater than 99%. The interspersion of these oligomers with a number of non-carboranyl monomers was performed. These monomers included linking groups (amines and thiols), fluorescent labels, a biotin derivative, and thymidine. These oligomers were isolated from from the synthesis support by treatment of the supported polymer with $NH_4OH$ for five minutes at room temperature. The water soluble oligomers were shown to contain closo-carboranes by $^{11}B$ NMR. Extended treatment of the oligomers with $NH_4OH$ (30 minutes at 80°) resulted in complete conversion of the boron cages to the nido-carborane analogues, as determined by $^{11}B$ NMR. These compounds have been shown to be of the correct composition by negative-ion electrospray mass-spectral measurements. The homogeneity of these oligomers was demonstrated by polyacrylamide gel electrophoresis (20% gel, 7M urea).

Phosphoramidite Monomer Synthesis

The phosphoramidite monomers required for oligophosphate synthesis in accordance with an aspect of the present invention are simple derivatives of diols. In a broad aspect of the present invention, almost any compound with two hydroxyl groups can be converted into an appropriate monomer. Dihydroxy compounds are converted into appropriate monomers by:

a) monoprotection with the dimethoxytrityl protecting group; and b) conversion of remaining hydroxyl group to the phosphoramidite by treatment with chloro β-cyanoethyl-N, N-diisopropylaminophosphite.

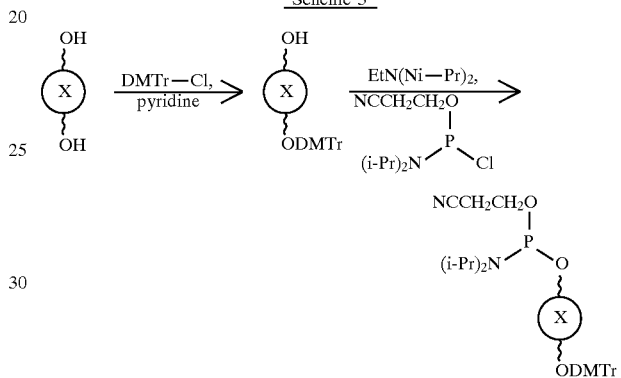

Scheme 3 shows a general example of a monomer synthesis in accordance with the present invention.

Boron-Rich Diol Synthesis

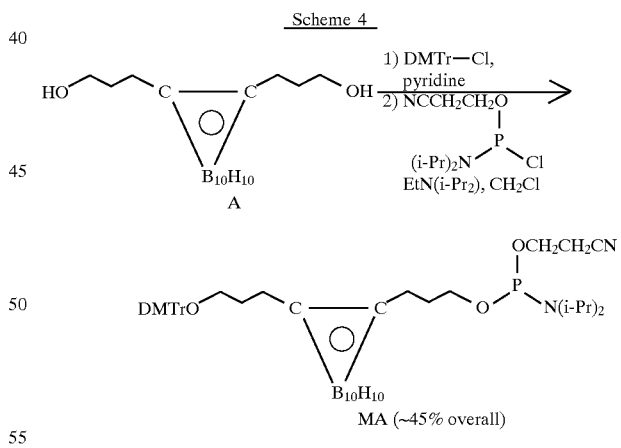

In accordance with a preferred embodiment of the present invention, the monomers used in-oligophosphate synthesis contain substantial quantities of boron. As such, certain aspects of this invention are related to methods for the production of boron-rich diols and compounds that can be converted into appropriate monomers (β-cyanoethyldiisopropylaminophosphoramidites) using the procedures of one aspect of the present invention.

The synthesis of boron-rich oligophosphates in accordance with the present invention uses boron-rich diols as the ultimate monomeric materials. In a preferred embodiment of the preseent invention, these diols are further derivatized to afford the starting materials for oligomer synthesis. The process for making a number of these diols is illustrated in the schematic formalism well-known to those of ordinary skill in the art.

PROCEDURES FOR DIOL SYNTHESIS

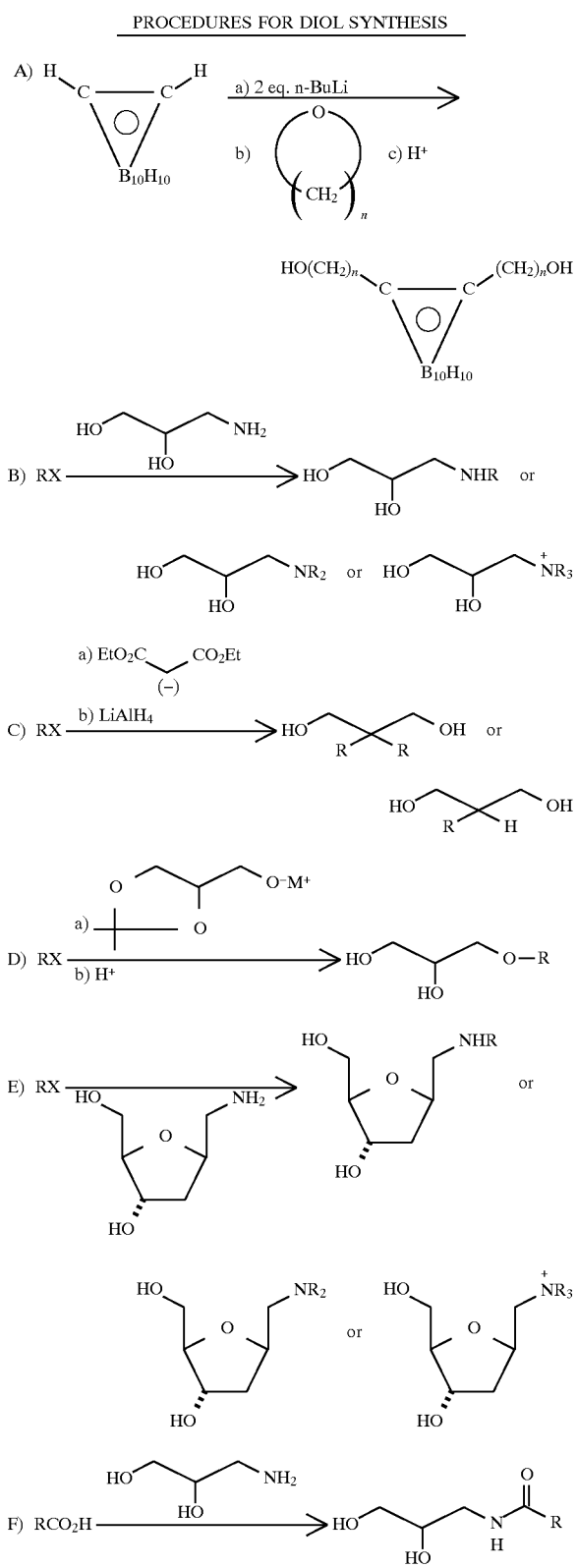

-continued
PROCEDURES FOR DIOL SYNTHESIS

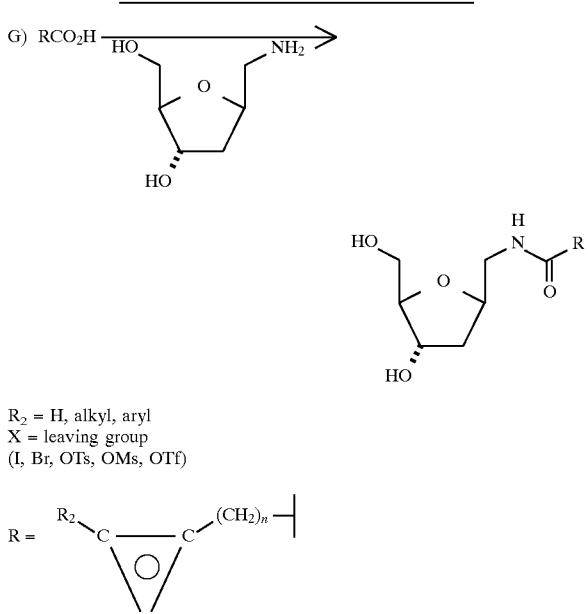

$R_2$ = H, alkyl, aryl
X = leaving group
(I, Br, OTs, OMs, OTf)

Delivery Systems

The oligomers described in accordance with certain aspects of the present invention may be used as agents for the concentration of boron in tumor cells for the boron neutron capture therapy of cancer. These oligomers may be suitable for use with a variety of targeting methods or delivery systems.

1. Unbound Delivery Strategies

The term "unbound" is used in accordance with an aspect of the present invention to indicate that no covalent bonds are formed between a boron-rich macromolecule formed in accordance with an aspect of the present invention and a delivery vehicle as specified in accordance with the teachings of the present invention.

A) Non-Targeted Tumor Preferential Accumulation of Macromolecules.

Macromolecules are known to accumulate preferentially in a tumor. As such, one aspect of the present invention uses such tendencies to direct macromolecules formed in accordance with the present invention to tumors independent of tumor-targeting delivery vehicles.

B) Liposomal Delivery.

Further to an aspect of the present invention, liposomes have been developed that may be used to deliver boron-rich molecules to tumor cells. Encapsulation of the boron-rich oligophosphates in liposomes is facilitated by the high water solubility of certain of the oligomers of the present invention. A further advantage of the present invention is that, for a number of these molecules, the diffusion of these macromolecules away from the tumor cells subsequent to delivery is substantially slowed in certain embodiments by virtue of their size.

C) Avidin/Biotin Based Delivery

Scheme 101

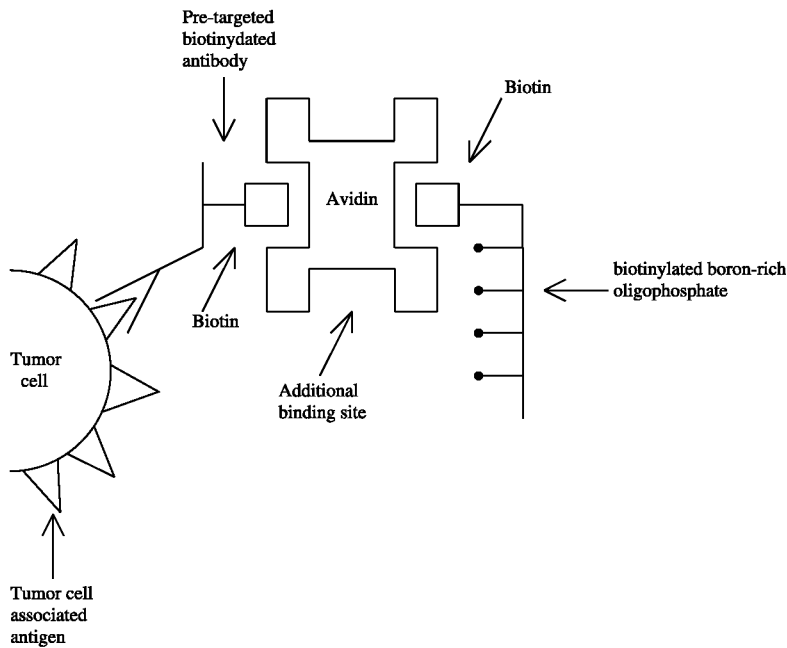

In accordance with the teachings of the present invention, Biotin-substituted oligomers are prepared either by attaching biotin residues during solid-phase synthesis (a number of reagents are commercially available for this very purpose) or by post-synthetic modification of functionalized oligomers with suitable biotin derivatives (e.g. via the reaction of amine-substituted oligomers with active esters of biotin). A preferred embodiment of the present invention uses the biotin/avidin interaction as a mode of delivery. The high affinity of this attraction as well as the tetrameric nature of avidin (or strepavidin), allows multiple oligomers to be localized by one avidin. In accordance with this embodiment, avidin is prelocalized in tumors. Several methods for accomplishing this goal are known. The overall concept is shown in Scheme 101.

D) Sense/Antisense Oligonucleotide-Based Delivery

In accordance with a further aspect of the present invention, sequences of DNA oligomers are appended to the boron-rich oligophosphates. This linking strategy is used in a preferred embodiment of the present invention, particularly with respect to the solid-phase synthesis, which is performed on instruments that are already optimized for the synthesis of DNA Scheme 102

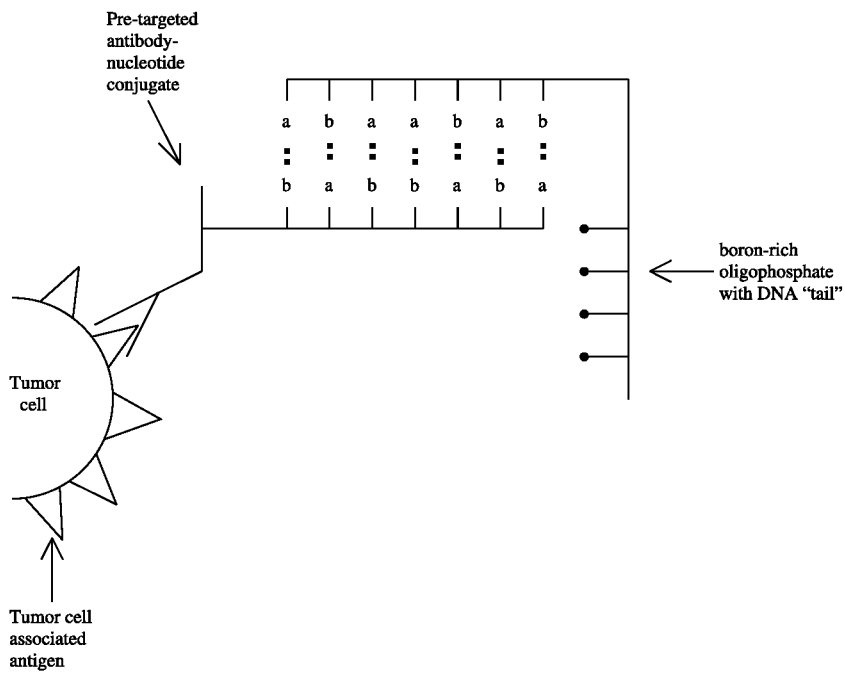

oligomers. A complementary strand of DNA is attached to the tumor targeting antibody. Scheme 102 gives a general description of this method.

2. Covalently Bound Delivery Systems

A) Synthesis of Reactive Oligomers

In accordance with the present invention, covalent bonds are formed between an oligomer and a delivery vehicle through the synthesis of oligomers containing reactive functional groups. Amine groups are extremely versatile functional handles for Scheme 103

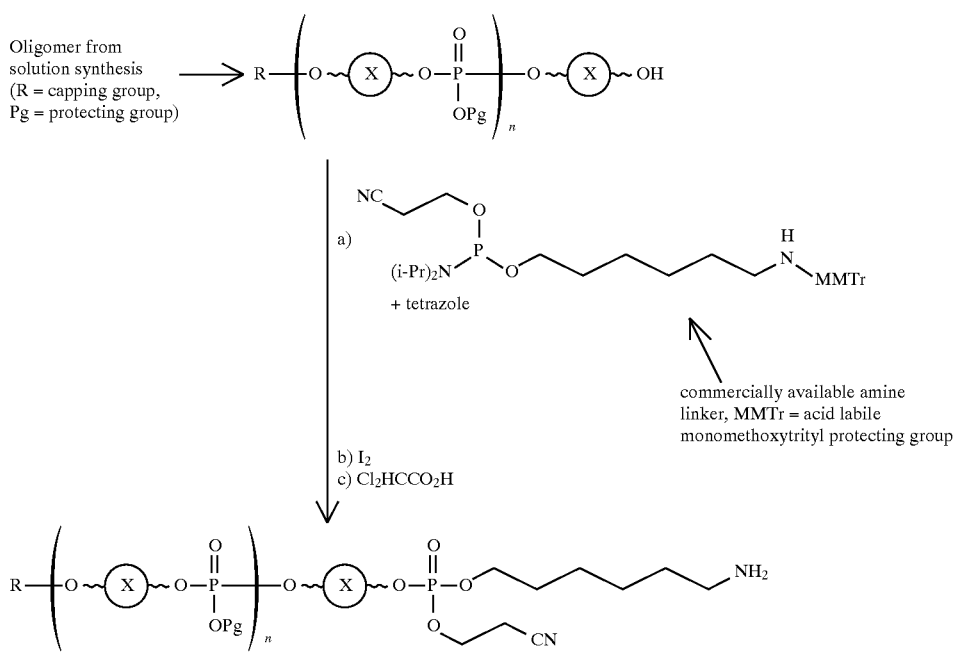

Scheme 104

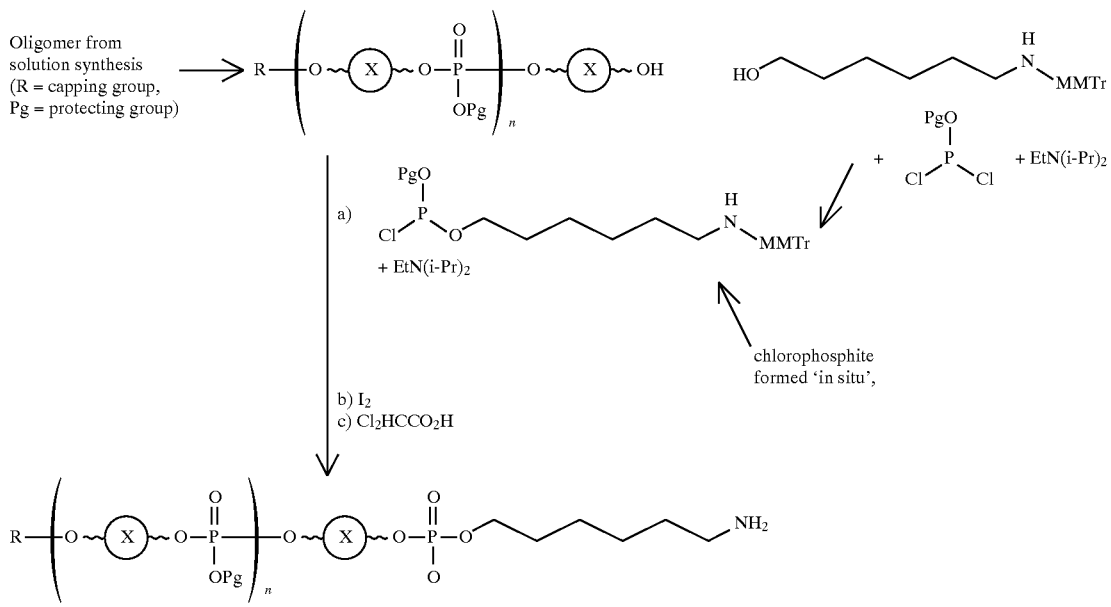

conjugation reactions. Terminal or internal amine groups can readily be incorporated during the solid-phase synthesis of the boron-rich oligophosphates in accordance with the present invention. Preferably, commercially available reagents are used for this purpose. The same reagents are used in accordance with a different aspect of the present invention to append amine groups to oligophosphates syn-thesized in solution (Scheme 103). In an alternative embodiment, protected amino-alcohols are used in the normal one-pot coupling reaction currently being used for the solution oligophosphate synthesis (Scheme 104).

Scheme 105

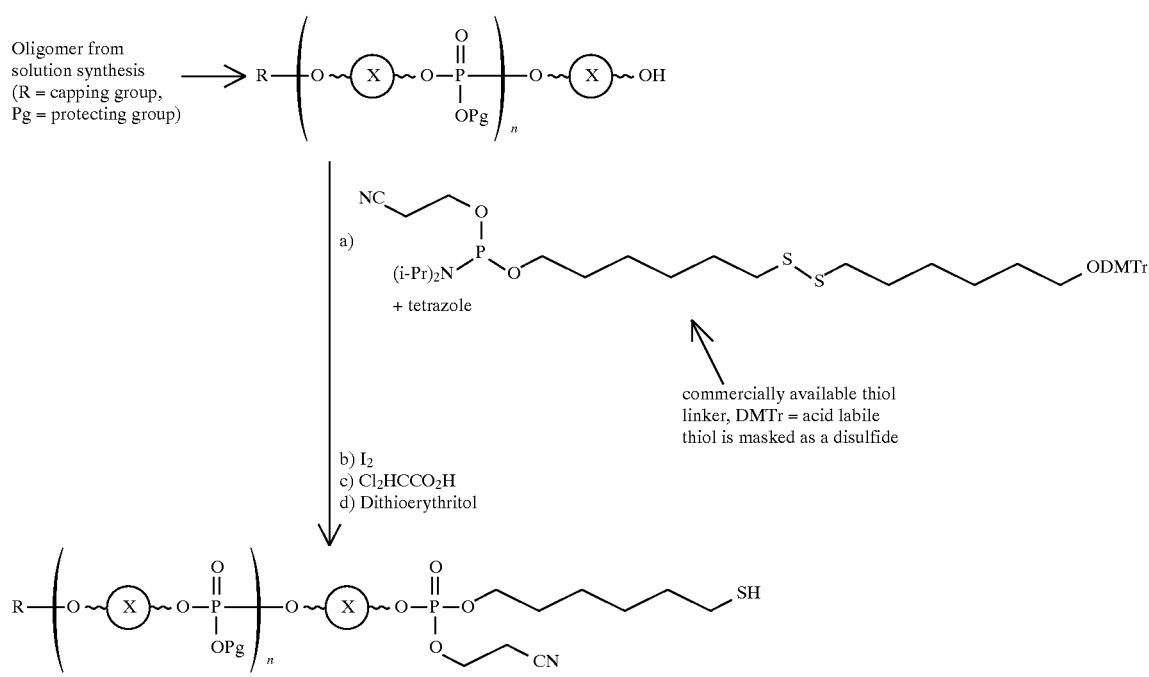

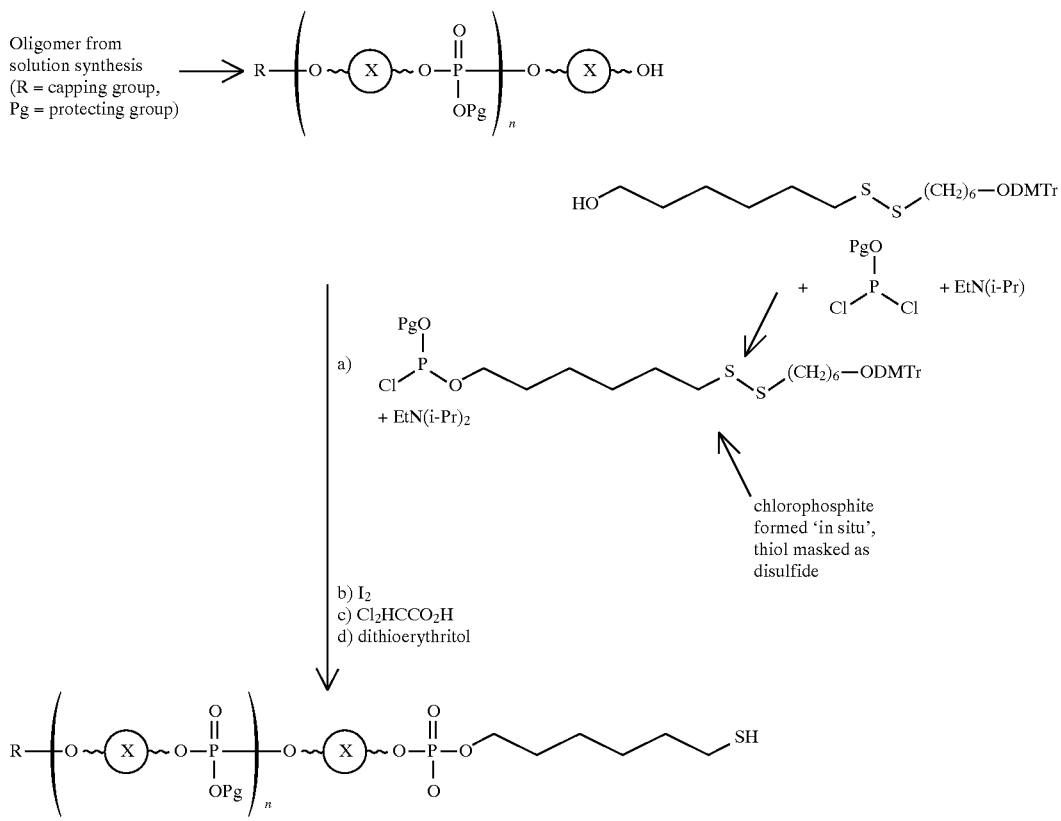

A second class of readily available functional handles used in accordance with the teachings of the present invention for attachment of delivery vehicles are the thiols. Although thiols are extremely reactive, they are remarkably selective. Again, it is preferable to use any of a number of commercial reagents to attach thiols to oligophosphates during solid-phase synthesis. These reagents can also be used to functionalize oligophosphates synthesized in solution (see Schemes 105 and 106). In accordance with an alternate embodiment of the present invention, thiols are introduced through the reaction of various amine-reactive thiolating reagents (such as Traut's Reagent, Scheme 107), which would convert amine-substituted oligomers to thiol substituted analogues. A third method for introducing reactive thiol handles on the oligophosphates would involve the synthesis of oligomers containing one or more phosphorothioate group (Scheme 108). In accordance with a preferred embodiment of the present invention, this class of compounds may routinely be made on solid-phase synthesis instruments or in solution.

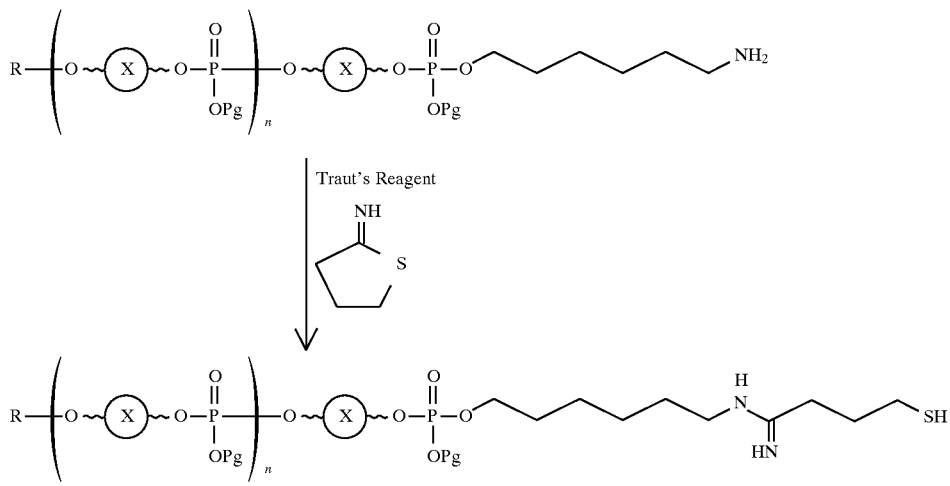

B) Conjugation Chemistry

With the oligophosphates fitted with reactive functional groups a number of different methods are used in accordance with the present invention to attach the oligophosphate to a desired delivery vehicle. The two main classes of conjugation reactions practiced in accordance with the present invention are those involving bifunctional linking molecules and those that involve direct conjugation.

i) Bifunctional crosslinking reagents. A large variety of bifunctional crosslinking reagents are either commercially available or easily synthesized and their chemistry is well known. Heterobifunctional crosslinking reagents are effective at coupling two components with similar reactive groups—a thiol containing boron-rich oligophosphate and a thiol containing targeting molecule, or an amine containing boron-rich oligophosphate and an amine containing targeting molecule.

be oxidatively coupled with another thiol, forming disulfide compounds. In another embodiment of the present invention, a disulfide bridged species is formed with a thiol exchange of a free thiol with an activated disulfide.

Conjugation Strategies for Tumor-Targeting Agents

In accordance with the present invention, immunoprotein based delivery systems are used to deliver boron-rich macromolecules, including whole monoclonal IgG molecules, IgG derived fragments (F(ab')$_2$ and Fab'), and smaller engineered fragments (Fab-SH 'single chain antibody'). The conjugation of boron-rich oligomers with these compounds could occur through free amine groups found on these proteins or through free thiols, either those revealed via antibody reduction, those created by amine modification, or those included in the design of engineered fragments. Another embodiment of the present invention uses an aldehyde at the conjugation site, which is revealed

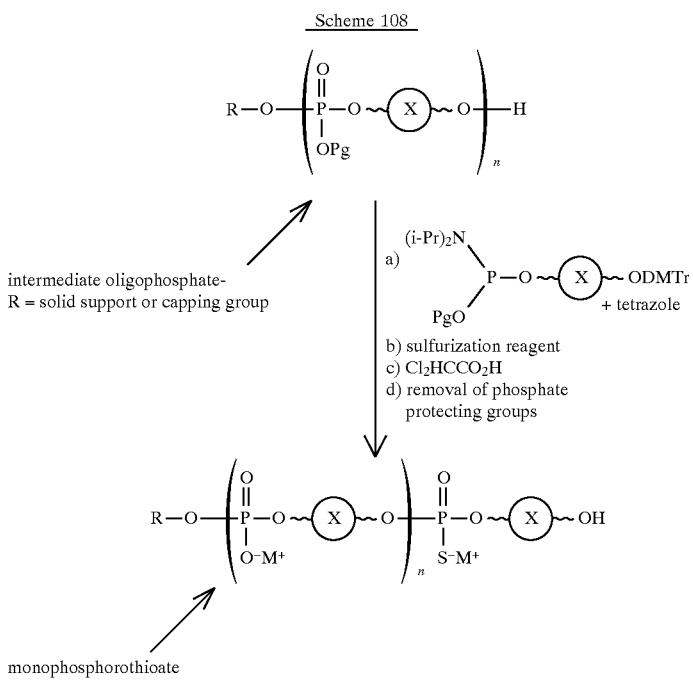

Homobifunctional crosslinking reagents are effective at coupling components with orthogonally reactive functional groups—amine containing boron-rich oligophosphates with thiol-containing targeting molecules, for example.

ii) Direct Conjugation. A multitude of methods are available for the direct conjugation of functionalized oligomers to tumor-targeting molecules. Amine containing oligomers can be readily coupled with active esters derived from carboxylic acids to form amides, with aldehydes to form Schiff Bases (and amines upon subsequent reduction), with epoxides to form β-hydroxy amines, and with carbons containing good leaving groups to form secondary, tertiary, or quaternary amines.

In accordance with a different aspect of the present invention, thiol containing oligomers are coupled directly to tumor-targeting molecules containing appropriate functional groups. Maleamides react very selectively with thiols at pH's around 6, and thiols readily alkylate electrophilic carbon centers (especially α-haloacetate esters and amides). In a different preferred embodiment, alkylation reactions are preformed with phosphorothioates. One preferred reaction mode using the thiol group takes advantage of its ability to upon oxidation of the carbohydrates found on intact IgG antibodies, which is then reacted with amine substituted oligomers.

Regulatory peptides may be also used as delivery vehicles in accordance with the present invention. These compounds are conjugated through their free amine groups or through endogeneous or created thiols. Other small molecules known to accumulate in tumors are conjugated with boron-rich oligophosphates by taking account of endogeneous binding sites. For example, amino-substituted oligomers are attached to free carboxyl groups found on porphyrins in accordance with a preferred embodiment. In general, the flexibility of the synthesis of the boron-rich oligomers allows for conjugation to a wide variety of molecules employing a spectrum of coupling strategies.

Boron-rich compounds are those that have more than ten percent by weight boron. In a preferred embodiment of the present invention, compounds with in excess of 20% boron by weight are preferred.

To achieve their full potential as $^{10}$B delivery vehicles, these building-block molecules must be enriched in the $^{10}$B-isotope. Enrichment to 95–96% $^{10}$B is commonly employed since the ultimate source of boron, boric acid, is commercially available at this level of isotope purity. All of the carborane molecules discussed herein can may be derived starting from boric acid, or more directly from $^{10}B_2H_6$. Accordingly, the production of enriched carboranes is readily achievable. The added cost of the enrichment process may be determinative in establishing which methodology is most cost-effective for production.

While the present invention has been described with reference to specific preferred embodiments thereof, it will be understood by those skilled in this art that various changes may be made without departing from the true spirit and scope of the invention. In addition, many modifications may be made to adapt the invention to a given situation without departing from its essential teachings.

What is claimed is:

1. A method of preparing a boron-rich oligophosphate comprising the steps of:
   (i) preparing a dihydroxy carborane derivative;
   (ii) converting said dihydroxy carborane derivative to a mono-hydroxy-protected dihydroxy carborane derivative;
   (iii) reacting said mono-hydroxy-protected dihydroxy carborane derivative with a coupling agent comprising phosphorus to form a protected monomer unit;
   (iv) converting said protected monomer unit to an alcohol by removing the hydroxy-protecting group; and,
   (v) reacting at least a plurality of said monomer units to form an oligophosphate.

2. The method of claim 1 in which a homogeneous oligophosphate is formed.

3. A method of preparing a boron-rich oligophosphate comprising the steps of:
   (i) forming a carboranyl diol;
   (ii) converting said diol to a mono-hydroxy-protected diol;
   (iii) converting said mono-hydroxy-protected diol to a protected phosphoramidite monomer;
   (iv) converting said protected phosphoramidite monomer to an alcohol by removing the hydroxy-protecting group; and,
   (v) reacting at least a plurality of said monomers to form an oligophosphate.

4. A method for forming a boron-rich oligophosphate comprising the steps of:
   (i) forming an o-carborane diol;
   (ii) converting said o-carborane diol to a mono-hydroxy-protected carboranyl diol;
   (iii) treating said mono-hydroxy-protected carboranyl diol with a phosphate coupling reagent thereby producing a mono-hydroxy-protected phosphotriester;
   (iv) converting the phosphotriester product in step (iii) to an alcohol by removing the hydroxy-protecting group; and
   (v) condensing said alcohol product in step (iv) with the mono-hydroxyl-protected diol produced in step (ii) using a phosphate coupling reagent to produce an oligophosphate.

5. The method for forming a boron-rich oligophosphate according to claim 4, wherein said step of treating said mono-hydroxy-protected carboranyl diol with a phosphate coupling reagent thereby producing a mono-hydroxy-protected phosphotriester further includes using isobutanol as an additional hydroxyl reactant.

\* \* \* \* \*

UNITED STATES PATENT AND TRADEMARK OFFICE
CERTIFICATE OF CORRECTION

PATENT NO. : 5,856,551
DATED : January 5, 1999
INVENTOR(S) : Robert R. Kane et al.

It is certified that error appears in the above-identified patent and that said Letters Patent is hereby corrected as shown below:

Column 1, line 8:

Before the "Background of the Invention," please add the following paragraph:

"This invention was made with Government support under Grant Numbers CA31753-09, CA53870-01 and CA09306-01 awarded by the National Institutes of Health. The Government has certain rights in this invention."

Signed and Sealed this

First Day of June, 1999

Attest:

Q. TODD DICKINSON

*Attesting Officer*     *Acting Commissioner of Patents and Trademarks*